United States Patent [19]

Nedelec et al.

[11] 4,258,039
[45] Mar. 24, 1981

[54] NOVEL 7-ALKYL-STEROIDS

[75] Inventors: Lucien Nedelec, Le Raincy; Vesperto Torelli, Maisons-Alfort; Robert Fournex, Paris; Colette Tournemine, Livry-Gargan, all of France

[73] Assignee: Roussel Uclaf, Paris, France

[21] Appl. No.: 125,891

[22] Filed: Feb. 29, 1980

[30] Foreign Application Priority Data

Mar. 22, 1979 [FR] France ................................ 79 07273

[51] Int. Cl.³ .......................... A61K 31/58; C07J 9/00
[52] U.S. Cl. ................................ 424/241; 260/239.57; 260/397.1
[58] Field of Search .................... 424/241; 260/239.57, 260/397.1

[56] References Cited

U.S. PATENT DOCUMENTS 3,787,394  1/1974  Arth et al. .................. 260/239.55 R

OTHER PUBLICATIONS

"Steroids", vol. 27, No. 6, pp. 759-769, article by Greenwell et al.

Primary Examiner—Elbert L. Roberts
Attorney, Agent, or Firm—Hammond, Littell, Weissenberger and Muserlian

[57] ABSTRACT

Novel 7-alkyl-$\Delta^4$-17$\alpha$-pregnene-3-ones of the formula

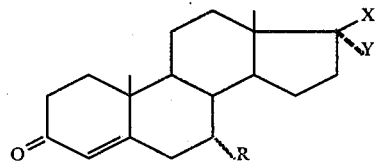

wherein R is selected from the group consisting of saturated and unsaturated alkyl of 2 to 8 carbon atoms, cycloalkyl alkyl of 4 to 8 carbon atoms and arylalkyl of 7 to 12 carbon atoms and X and Y form the group

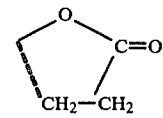

or X is OH and Y is

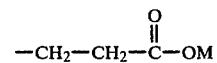

and M is selected from the group consisting of hydrogen, alkali metal and NH₄ and the wavy line indicates the α- or β-position or mixtures thereof having aldosterone antagonistic activity and increased hydrosodium diuresis with organic potassium conservation while devoid of secondary hormonal effects and their preparation.

34 Claims, No Drawings

NOVEL 7-ALKYL-STEROIDS

STATE OF THE ART

Related compounds are described in U.S. Pat. No. 3,845,041 and Atwater et al [J. Org. Chem., Vol. 26(9) (1961)], Grunwell et al [Steroids, 27(6) June, 1976] and J. Chem. Soc., Vol. 26 (1961), p. 3077–83.

OBJECTS OF THE INVENTION

It is an object of the invention to provide the novel 7-alkyl-steroids of formula I and a novel process for the preparation thereof.

It is another object of the invention to provide novel aldosterone antagonistic compositions and to a novel method of treating arterial hypertension and cardiac insufficiencies.

These and other objects and advantages of the invention will become obvious from the following detailed description.

THE INVENTION

The novel products of the invention are 7-alkyl-$\Delta^4$-17α-pregnene-3-ones of the formula

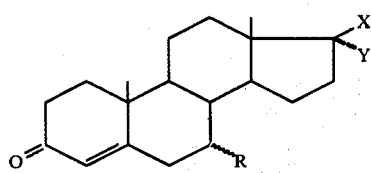

I wherein R is selected from the group consisting of saturated and unsaturated alkyl of 2 to 8 carbon atoms, cycloalkyl alkyl of 4 to 8 carbon atoms and arylakyl of 7 to 12 carbon atoms and X and Y form the group

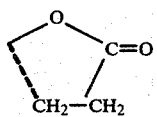

or X is OH and Y is

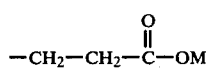

and M is selected from the group consisting of hydrogen, alkali metal and NH$_4$ and the wavy line indicates the α- or β-position or mixtures thereof.

Examples of R are alkyl of 2 to 8 carbon atoms such as ethyl, propyl, isopropyl, butyl, isobutyl, tert.-butyl, n-pentyl, n-hexyl, 2-methylpentyl, 2,3-dimethylbutyl and n-heptyl; unsaturated alkyl of 2 to 8 carbon atoms such as vinyl, isopropenyl, allyl, 2-methyl-allyl, butenyl or isobutenyl; cycloalkylalkyl of 4 to 8 carbon atoms such as cyclopropylalkyl such as cyclopropylmethyl or cyclopropylethyl and arylalkyl of 7 to 12 carbon atoms, preferably benzyl. M may be hydrogen, NH$_4$ or an alkali metal such as sodium, potassium or lithium.

Among the preferred compounds of the invention are those wherein X and Y are the group

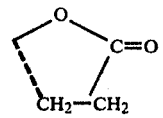

as well as those wherein X is OH and Y is —CH$_2$—CH$_2$—COOK. Also preferred are the compounds of formula I wherein R is in the 7α-position and R is ethyl, n-propyl, n-butyl, 2-methylpropyl, vinyl or allyl. Specific preferred compounds are potassium 7α-propyl-$\Delta^4$-17α-pregnene-17β-ol-3-one-21-carboxylate and γ-lactone of 7α-propyl-$\Delta^4$-17α-pregnene-17β-ol-3-one-21-carboxylic acid.

The novel process of the invention for the preparation of compounds of formula I comprises reacting a compound of the formula

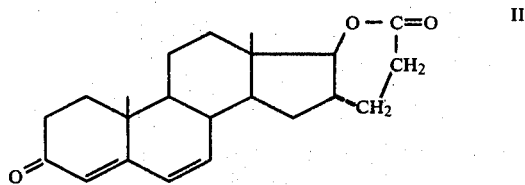

II with a compound of the formula

R—Mg—Hal

III wherein R has the above definition and Hal is halogen in the presence of a cuprous salt or a compound of the formula (R)$_2$-CuLi

IV and then with an acid to obtain a compound of the formula

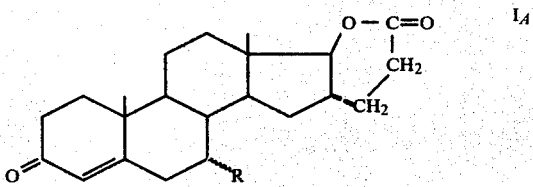

I$_A$ in the form of a mixture of 7α and 7β-isomers which may be separated, if desired, and the mixture or the individual isomers is reacted with an alkali metal hydroxide or ammonium hydroxide to obtain a compound of the formula

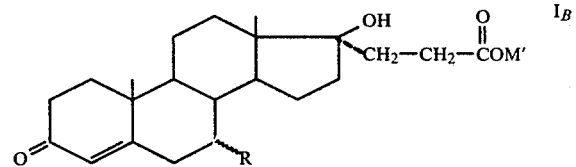

I$_B$ wherein R has the above definition and M' is alkali metal or NH$_4$ in the form of 7α or 7β-isomers or mixtures thereof which may be separated, if desired, and the latter may be reacted with an acid to form the corresponding compound of formula I$_B$ wherein M' is hydrogen.

In a preferred mode of the process of the invention, the X or RMgX is chlorine, bromine or iodine and the cuprous salt is the cuprous chloride, bromide or iodide. The acid is a strong acid such as hydrochloric acid, nitric acid or sulfuric acid. The separation of the mixtures of isomers may be effected with chromatography or fractional crystallization. The preferred alkali metal hydroxide for reacting with a compound of formula $I_A$ is sodium hydroxide or potassium hydroxide. The acid agent used to treat the compound of formula $I_B$ is preferably hydrochloric acid, sulfuric acid, nitric acid or acetic acid.

The starting compound of formula II is described in U.S. Pat. No. 3,194,803.

The novel aldosterone antagonistic compositions of the invention are comprised of antagonistically effective amount of at least one compound of formula I and an inert pharmaceutical carrier or excipient. The compositions may be in the form of tablets, coated tablets, cachets, capsules, granules, emulsions, syrups, suppositories and injectable solutions or suspensions.

Examples of suitable excipients are talc, arabic gum, lactose, starch, magnesium stearate, cacao butter, aqueous or non-aqueous vehicles, fatty bodies of animal or vegetable origins, paraffinic derivatives, glycols, diverse wetting agents, dispersants or emulsifiers or preservatives.

The compositions of the invention possess aldosterone antagonistic activity and increased hydrosodium diuresis with organic potassium conservation. The compositions have the further advantage of being devoid of secondary hormonal effects, especially anti-androgenic and anti-estrogenic activity. They are useful for the treatment of arterial hypertension and cardiac insufficiencies.

The novel method of the invention of treating cardiac insufficiencies and arterial hypertension in warm-blooded animals, including humans, comprises administering to warm-blooded animals an amount of at least one compound of formula I sufficient to treat arterial hypertension and cardiac insufficiencies. The compounds may be administered rectally, orally, transcutaneously or intraveinously and the usual daily dose is depending on the compound and method of administration and may be from 0,2 mg to 20 mg/kg per day in the adult by oral route.

In the following examples there are described several preferred embodiments to illustrate the invention. However, it should be understood that the invention is not intended to be limited to the specific embodiments.

EXAMPLE 1

γ-lactone of 7α-ethyl-Δ⁴-17α-pregnene-17β-ol-3-one-21-carboxylic acid

A mixture of 2.86 g of cuprous iodide and 5.25 ml of n-butylsulfide was stirred at room temperature until total dissolution occured with slight exothermic reaction or about 10 minutes and a solution of 10.2 g of the γ-lactone of Δ⁴,⁶-17α-pregnadiene-17β-ol-3-one-21-carboxylic acid (canrenone) in 150 ml of anhydrous tetrahydrofuran was added to the resulting complex. The resulting solution was cooled to −30° C. and a mixture of 54 ml of an ether solution of 0.9 M of ethyl magnesium bromide, 50 ml of ether and 50 ml of tetrahydrofuran was added thereto with strong stirring over 75 minutes. The mixture was stirred at −30° C. for 60 minutes and then was acidified with 120 ml of 2 N hydrochloric acid. The mixture was stirred at room temperature for 60 minutes and the decanted organic phase washed with water, dried and evaporated to dryness. The crystalline residue was chromatographed over silica gel and was eluted with a 3-2 cyclohexaneethyl acetate mixture to obtain 6.3 of γ-lactone of 7α-ethyl-Δ⁴-17α-pregnene-17β-ol-3-one-21-carboxylic acid melting at 167° C. and a specific rotation of $[\alpha]_D^{20} = +67° \pm 1.5°$ (c=1% in chloroform). Crystallization from methanol did not change the melting point.

Also obtained were 3.2 g of the γ-lactone of 7β-ethyl-Δ⁴-17α-pregnene-17β-ol-3-one-21-carboxylic acid melting at 150° C. and then 170° C. After crystallization from methanol, the product melted at 155° C. and then 172° C. after solidification and had a specific rotation of $[\alpha]_D^{20} = +62.5° \pm 1.5°$ (c=1% in chloroform).

EXAMPLE 2

γ-lactone of 7α-propyl-Δ⁴-17α-pregnene-17β-ol-3-one-21-carboxylic acid

A complex was formed by stirring a mixture of 382 mg of cuprous iodide and 0.7 ml of n-butylsulfide at room temperature and a solution of 5.1 g of canrerone and 75 ml of anhydrous tetrahydrofuran and 50 ml of anhydrous ether was added thereto. The mixture was cooled to −20° C. and an ether solution of 1.2 M of propyl magnesium bromide were added thereto with good stirring over 35 minutes. The mixture was stirred at −20° C. for another 10 minutes and the resulting yellow suspension was acidified with 50 ml of 5 N hydrochloric acid. The mixture was stirred at room temperature for 30 minutes and was then extracted with ethyl acetate. The organic phase was washed with water, with 0.2 N sodium thiosulfate solution, then with water, was dried over sodium sulfate and evaporated to dryness. The oily residue was chromatographed over silica gel and was eluted with a 1-4 benzene-ether mixture to obtain 3.3 g of γ-lactone of 7α-propyl-Δ⁴-17α-pregnene-17β-ol-3-one-21-carboxylic acid which after crystallization from methanol melted at 205° C. and had a specific rotation of $[\alpha]_D^{20} = +70° \pm 1.5°$ (c=1% in chloroform) and 1.4 g of amorphus 7β-isomer thereof.

EXAMPLE 3

Potassium 7α-propyl-Δ⁴-17α-pregnene-17β-ol-3-one-21-carboxylate

A mixture of 1.15 g of the product of Example 2, 5.4 ml of ethanolic 0.53 N potassium hydroxide solution and 5.4 ml of water was refluxed for 15 minutes and was then concentrated to a small volume under reduced pressure to obtain a thick yellow syrup. 50 ml of acetone were added to the mixture and the potassium salt precipitated. The mixture was vacuum filtered and the recovered product was washed with acetone and dried at 50° C. The raw product was crystallized by dissolution in 1.3 ml of water to which was added 19.5 ml of acetone to obtain 1 g of potassium 7α-propyl-Δ⁴-17α-pregnene-17β-ol-3-one-21-carboxylate in the form of colorless needles solvated with one molecule of water. The product melted towards 290° C. (Maquenne block) and had a specific rotation of $[\alpha]_D^{20} = +48° \pm 1.5°$ (c=1% in water).

EXAMPLE 4

γ-lactone of
7α-butyl-Δ$^4$-17α-pregnene-17β-ol-3-one-21-carboxylic acid

A complex formed by stirring a mixture of 191 mg of cuprous iodide and 0.35 ml of n-butylsulfide was dissolved in 35 ml of anhydrous tetrahydrofuran and 1.7 g of canrenone was added thereto. The solution was stirred on an ice bath (interior temperature towards +5° C.) and 7.5 ml of an ether solution of 1.2 M of butyl magnesium bromide were slowly added over 30 minutes. The mixture was stirred for 30 minutes and was acidified with a large excess of 5 N hydrochloric acid as in Example 2. The mixture was chromatographed over silica gel and was eluted with a 3–2 cyclohexane-ethyl acetate mixture to obtain a crystalline product which was triturated with isopropyl ether, vacuum filtered and air dried to obtain 1.12 g of γ-lactone of 7α-butyl-Δ$^4$-17α-pregnene-17β-ol-3-one-21-carboxylic acid melting at 147° C. After crystallization from methanol, the product melted at 149° C. and had a specific rotation of $[\alpha]_D^{20} = +54°\pm1°$ (c=1% in chloroform). Also obtained was 0.65 g of the 7β-isomer in an amorphous form.

EXAMPLE 5

Potassium
7α-butyl-Δ$^4$-17α-pregnene-17β-ol-3-one-21-carboxylate

A mixture of 1.19 g of the product of Example 4, 5.4 ml of water and 5.4 ml of ethanolic 0.53 N potassium hydroxide solution was refluxed for 15 minutes and the mixture was concentrated to a thick, slightly yellow syrup. 50 ml of acetone were added to the syrup during which the potassium salt crystallized as fine needles and the mixture was vacuum filtered. The recovered product was rinsed with acetone, dried at 50° C. and was dissolved in 3 ml of 50% aqueous acetone. 28.5 ml of acetone were added thereto to obtain 1.13 g of potassium 7α-butyl-Δ$^4$-17α-pregnene-17β-ol-3-one-21-carboxylate of colorless needles solvated with 2 molecules of water melting towards 260° C. (Maquenne) and a specific rotation of $[\alpha]_D^{20} = +36.5°\pm1.5°$ (c=1% in water).

EXAMPLE 6

γ-lactone of
7α-(2-methyl-propyl)-Δ$^4$-17α-pregnene-17β-ol-3-one-21-carboxylic acid A complex obtained by stirring 135 mg of cuprous iodide and 0.25 ml of n-butylsulfide was dissolved in 15 ml of anhydrous tetrahydrofuran and 680 mg of canrenone were added thereto. The resulting solution was cooled to −30° C. and 4.3 ml of an etheral 0.7 M isobutyl magnesium bromide solution was added thereto dropwise with good stirring over 20 minutes. The mixture was stirred at 30° C. for another 15 minutes and the mixture was turned from an orange-red to yellow brown. The mixture was acidified with a large excess of 2 N hydrochloric acid and the mixture was stirred at room temperature for 30 minutes. The mixture was extracted with ethyl acetate and the organic phase was washed with water, dried and evaporated to dryness. The residue was chromatographed over silica gel and was eluted with a 1–9 benzene-ether mixture to obtain first 450 mg of product which was crystallized from 1 ml of methanol to obtain 320 mg of γ-lactone of 7α-(2-methyl-propyl)-Δ$^4$-17α-pregnene-17β-ol-3-one-21-carboxylic acid as crystals solvated with 0.5 moles of methanol melting at 190° C. and towards 100° C. after dessolvation and having a specific rotation of $[\alpha]_D^{20} = +63°\pm1.5°$ (c=1% in chloroform). Also recovered was 310 mg of the corresponding 7β-isomer which was crystallized from methylene chlorideisopropyl ether to obtain 230 mg of the β-isomer melting at 218° C. and having a specific rotation of $[\alpha]_D^{20} = +79°\pm1.5°$ (c=1% in chloroform).

EXAMPLE 7

γ-lactone of
7α-ethenyl-Δ$^4$-17α-pregnene-17β-ol-3-one-21-carboxylic acid

A complex formed by stirring a mixture of 2.1 g of cuprous iodide and 5.6 ml of n-butylsulfide at room temperature was dissolved in a solution of 10 g of canrenone in 200 ml of anhydrous tetrahydrofuran and the solution was cooled to −20° C. 44 ml of a solution of N vinyl magnesium chloride in tetrahydrofuran were added dropwise to the mixture with good stirring over 80 minutes. The mixture was stirred at −20° C. for another 60 minutes and the suspension was acidified with 45 ml of 2 N hydrochloric acid. The mixture was stirred at room temperature for 90 minutes and was then extracted with ethyl acetate. The organic phase was washed with water, with aqueous 0.2 M sodium thiosulfate, dried and evaporated to dryness. The oily residue was chromatographed over silica gel and was eluted with a 1—1 cyclohexane-ethyl acetate mixture to obtain first 2.9 g of γ-lactone of 7α-ethenyl-Δ$^4$-17α-pregnene-17β-ol-3-one-21-carboxylic acid melting at 199° C. and after crystallization from isobutyl acetate and then from ethanol melted at 75° C. and had a specific rotation of $[\alpha]_D^{20} = +17.5°\pm1.5°$ (c=1% in chloroform) and second, 3.5 g of the corresponding 7β-isomer which after crystallization from a methylene chloride-isopropylether mixture melted towards 100° C., then at 142° C. and 161° C.

EXAMPLE 8

γ-lactone of
7α-(2-propenyl)-Δ$^4$-17α-pregnene-17β-ol-3-one-21-carboxylic acid

Using the procedure of House et al [J. Org. Chem., Vol. 33 (1968)], p. 949, a mixture of 475 mg of cuprous iodide and 0.875 ml of n-butylsulfide was stirred at room temperature until the cuprous salt dissolved with a slight exothermal result which was total in 10 minutes and the resulting orange yellow liquid cuprous complex was dissolved in 10 ml of anhydrous ethanol(solution A).

Using the procedure of Seyferth et al [J. Org. Chem., Vol. 26 (1961), p. 4797] and Whitesides et al [J.A.C.S., Vol. 91 (1969), p. 4871], 2.85 ml of a solution of 1.75 M of phenyllithium in a 7–3 benzene-ether mixture were added with stirring to a solution of 1.95 g of triphenylallyletain in 15 ml of anhydrous ether and an abundant white precipitate of tetraphenyletain was formed. The suspension was stirred for another 15 minutes and was then cooled to −30° C. Solution A was then added thereto over 10 minutes and the mixture was stirred for another 15 minutes to obtain a solution of lithium diallylcuprate with tetraphenyletain suspended therein.

A solution of 680 mg of canrenone in 25 ml of anhydrous tetrahydrofuran was added to the said solution and the mixture was stirred at −30° C. for 90 minutes and was then acidified with 15 ml of 2 N hydrochloric acid. The mixture was stirred at room temperature for 2 hours and was then filtered to remove tetraphenyletain. The decanted organic phase was washed with water, dried and evaporated to dryness and the residue was chromatographed over silica gel. Elution with a 95–5 chloroform-ethyl acetate mixture yielded 408 mg of γ-lactone of 7α-(2-propenyl)-Δ$^4$-17α-pregnene-17β-ol-3-one-21-carboxylic acid melting at 184° C. and then 194° C. after resolidification. An analytical sample after crystallization from methanol melted at 196° C. and had a specific rotation of $[\alpha]_D^{20} = +113° \pm 3°$ (c=0.7% in chloroform).

EXAMPLE 9

γ-lactone of 7α-(3-butenyl)-Δ$^4$-17α-pregnene-17β-ol-3-one-21-carboxylic acid 10 ml of a solution of 9.05 g of chloromethyl cyclopropane in 75 ml of ether was added with stirring to a mixture of 3 g of magnesium turnings in 25 ml of ether. When a reaction started, the rest of the solution was added over 40 minutes while maintaining reflux and the mixture was then refluxed with stirring for 30 minutes and then was allowed to stand while cooling to room temperature (solution A).

A complex was formed by dissolution of 135 mg of cuprous chloride and 85 mg of lithium chloride in 35 ml of tetrahydrofuran and 1.7 g of canrenone were added thereto and after dissolution occurred, the solution was cooled to −30° C. 14.2 ml of solution A were added thereto with stirring over 30 minutes and was stirred at −30° C. for 15 minutes. 15 ml of 5 N hydrochloric acid were added to acidify the mixture and the mixture was allowed to rise to room temperature. The mixture was stirred until 2 liquid phases appeared and was then extracted with ethyl acetate. The organic phase was washed with water, an aqueous sodium chloride solution, dried and evaporated to dryness. The residue was chromatographed over silica gel and was eluted with a 3–1 ether-benzene mixture to obtain 1.25 g of γ-lactone of 7α-(3-butenyl)-Δ$^4$-17α-pregnene-17β-ol-3-one-21-carboxylic acid which after crystallization from isopropanol or ethyl acetate melted at 180° C. and had a specific rotation of $[\alpha]_D^{20} = +58° \pm 1.5°$ (c=1% in chloroform).

Analysis: $C_{26}H_{36}O_3$; molecular weight=396.57; Calculated: %C 78.74, %H 9.15; Found: %C 78.9, %H 9.0.

Also obtained was 0.5 g of the 7β-isomer which after crystallization from isopropanol melted at 132° C. and had a specific rotation of $[\alpha]_D^{20} = +64° \pm 1.5°$ (c=1% in chloroform).

Analysis: $C_{26}H_{36}O_3$; molecular weight=396.57; Calculated: %C 78.74, %H 9.15; Found: %C 78.5, %H 9.0.

EXAMPLE 10

Potassium 7α-(3-butenyl)-Δ$^4$-17α-pregnene-17β-ol-3-one-21-carboxylate 7 ml of water and 3.5 ml of ethanolic 1.38 N potassium hydroxide were added to 2 g of the 7α-isomer of Example 9 and the mixture was refluxed for 30 minutes and was evaporated to dryness. Acetone was added to the residue and the mixture was vacuum filtered. The product was washed with acetone and was dried to obtain 2.2 g of potassium 7α-(3-butenyl)-Δ$^4$-17α-pregnene-17β-ol-3-one-21-carboxylate with a specific rotation of $[\alpha]_D^{20} = +39° \pm 1°$ (c=1% in water).

Analysis: $C_{26}H_{37}O_4K$. 1.25 $H_2O$; Calculated: %C 65.72, %H 8.38; Found: %C 65.7, %H 8.3.

EXAMPLE 11

γ-lactone of 7α-benzyl-Δ$^4$-17α-pregnene-17β-ol-3-one-21-carboxylic acid

A solution of 1.7 g of canrenone in 30 ml of tetrahydrofuran was added to a complex formed of 135 mg of cupric chloride, 84 mg of lithium chloride and 5 ml of tetrahydrofuran and after cooling the mixture to about 0° C., 14.3 ml of a solution of 0.7 M of benzyl magnesium bromide in ether were added thereto over 40 minutes. The mixture was acidified with 10 ml of 5 N hydrochloric acid and the mixture was stirred at room temperature for one hour and was diluted with water. The mixture was extracted with ethyl acetate and the organic phase was washed with water, with aqueous saturated sodium chloride solution, dried and evaporated to dryness. The residue was chromatographed over silica gel and was eluted with a 7–3 benzene-ethyl acetate mixture to obtain 1.2 g of γ-lactone of 7α-benzyl-Δ$^4$-17α-pregnene-17β-ol-3-one-21-carboxylic acid which after crystallization from methyl ethyl ketone melted at 258° C. and had a specific rotation of $[\alpha]_D^{20} = +2.5° \pm 1°$ (c=1% in chloroform). 0.15 g of the 7β-isomer were obtained which after crystallization from ethanol melted at 220° C.

EXAMPLE 12

Tablets were prepared containing 50 mg of product of Example 2 or 30 mg of the product of bxample 3 and sufficient excipient of talc, starch and magnesium stearate for a final weight of 400 mg.

PHARMACOLOGICAL DATA

A. Anti-aldosterone Activity

The test was effected by a test inspired by Kagawa [P.S.E.M.B., Vol. 99 (1958), p. 705] and Marcus [Endocrinology, Vol. 50 (1952), p. 286] using male Sprague Dawley SPF IFFA CREDO rats weighing 180 g. The rats were surrenalectomized 7 days before diuresis while anesthesized with Imalgene (Ketamine) by intraperitoneal administration at 100 mg/kg. After the operation and just before the start of the test, the rats received water with physiological serum and 16 hours before the start of the test, the physiological serum was replaced with water containing 5% glucose. The test products were administered orally one hour before being placed in a cage. At the moment of the start of diuresis, the animals received intraperitoneally a hydrosaline surcharge of 5 ml per rat of 9% physiological serum and subcutaneously 1 µg/Kg of aldosterone monoacetate in 2.5% alcoholic solution. The rats were placed in pairs in a diuresis cage without food or drink for 4 hours. At that time, a forced emission was effected by pressure on the vessels and measured the urine recovered. After careful rinsing of the cages and glass, the volume of urine was adjusted to 50 ml and with the said solution, the amount of sodium and potassium in the urine was determined by photometry with a flame autoanalyzer. The results expressed as a percentage of activity inhibition of 1 µg/Kg of aldosterone monoacetate injected subcutaneously with the log of ratio sodium concentration/potassium concentration by the method of Kagawa [Endocrinology, Vol. 67 (1967), p. 125–132] are reported in Table I.

TABLE I

| Product of Example | Oral dose in mg/kg | % inhibition |
|---|---|---|
| 2 | 2 | 47 |
| γ-lactone of 7α-methyl-Δ⁴-17α-pregnene-17β-ol-3-one-21-carboxylic acid | 2 | 27 |

The results of Table I shows that product of Example 2 is almost twice as active as the corresponding 7α-methyl compound.

Using the same procedure with the compound of Example 3 at a dose of 0.4 mg/kg, the percentage of inhibition was 58% which is a very good antialdosterone activity.

B. Androgenic Activity

The prostate, removed from male rats castrated 24 hours earlier, was homogenized in a buffered 10 millimoles tromethamine containing 0.25 M saccharoses and hydrochloric acid at a pH of 7.4. The homogenate was centrifuged at 105,000 g for one hour and the surnagent liquid or cytosol was adjusted with a 1/5 dilution (weight/volume). The cytosol was incubated at 0° C. for 2 hours with a fixed concentration of tritiated 17α-methyl-Δ$^{4,9,11}$-estratriene-17β-ol-3-one designated as tritiated R in the presence or absence of increasing concentration of the same cold product called cold R product, of testosterone or test product.

The radioactivity of the tritiated product was determined over 2 hours given off by the technique of absorption of carbon-dextran (1.25%–0.625%). The curves representing the percentages of tritiated R product bound as a function of the log of concentration of the cold R product, of testosterone or the test product and the I$_{50}$ straight parallel to the axis of the abcisses and the ordinate $$\frac{B}{T} = \frac{B/T \text{ max.} + B/T \text{ min.}}{2}$$

B/T max is the percentage of tritiated R product bound when the product is not added.
B/T min. is the percentage of tritiated R product bound when the maximum quantity of cold R product is added.

The intersection of this I$_{50}$ straight line and the curves determine the values CT and CX wherein CT is the concentration of cold testosternone which inhibits by 50% the fixation of the tritiated R product and CX is the concentration of test compound which inhibits by 50% the fixation of tritiated R product. The relative affinity of the test compound or ARL is determined by the formula $$ARL = 100 \times \frac{CT}{CX}$$

The results are reported in Table II.

TABLE II

| Product of Example | ARL |
|---|---|
| Testosterone | 100 |
| 2 γ-lactone of 7α-methyl-Δ⁴-17α-pregnene-17β-ol-3-one- | 0.4 |

TABLE II-continued

| Product of Example | ARL |
|---|---|
| 21-carboxylic acid | 28 |

The product of Example 2 was practically devoid of affinity for prostatic reception of testosterone while γ-lactose of 7α-methyl-Δ⁴-17α-pregnene-17β-ol-3-one-21-carboxylic acid showed a sufficiently clear affinity for prostatic reception of testosterone. Under the same conditions, the product of Example 3 had an ARL of 0.2 which shows a definitely inferior affinity to that of the product of Example 2 for prostatic reception of testosterone.

Various modifications of the products and processes of the invention may be made without departing from the spirit or scope thereof and it is to be understood that the invention is to be limited only as defined in the appended claims.

We claim:
1. 7-alkyl-Δ⁴-17α-pregnene-3-ones of the formula

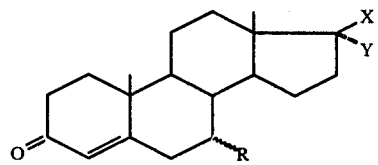

wherein R is selected from the group consisting of saturated and unsaturated alkyl of 2 to 8 carbon atoms, cycloalkyl alkyl of 4 to 8 carbon atoms and arylalkyl of 7 to 12 carbon atoms and X and Y form the group

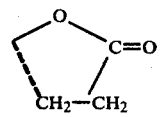

or X is OH and Y is

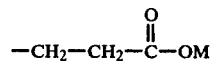

and M is selected from the group consisting of hydrogen, alkali metal and NH$_4$ and the wavy line indicates the α- or β-position or mixtures thereof.

2. A compound of claim 1 wherein X and Y form the group

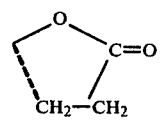

3. A compound of claim 1 wherein X is —OH and Y is

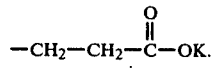

4. A compound of claims 1, 2 or 3 wherein R is in the α-position.

5. A compound of claim 1 wherein R is selected from the group consisting of ethyl, n-propyl, n-butyl, 2-methylpropyl, allyl and vinyl.

6. A compound of claim 5 wherein R is in the α-position.

7. A compound of claim 1 which is potassium 7α-propyl-Δ⁴-17α-pregnene-17β-ol-3-one-21-carboxylate.

8. A compound of claim 1 which is the γ-lactone of 7α-propyl-Δ⁴-17α-pregnene-17β-ol-3-one-21-carboxylic acid.

9. A compound of claim 1 which is the γ-lactone of 7α-ethyl-Δ⁴-17α-pregnene-17β-ol-3-one-21-carboxylic acid.

10. A compound of claim 1 which is the γ-lactone of 7α-butyl-Δ⁴-17α-pregnene-17β-ol-3-one-21-carboxylic acid.

11. A compound of claim 1 which is the γ-lactone of 7α-(2-methylpropyl)-Δ⁴-17α-pregnene-17β-ol-3-one-21-carboxylic acid.

12. A compound of claim 1 which is the γ-lactone of 7α-ethenyl-Δ⁴-17α-pregnene-17β-ol-3-one-21-carboxylic acid.

13. A compound of claim 1 which is the γ-lactone of 7α-(2-propenyl)-Δ⁴-17α-pregnene-17β-ol-3-one-21-carboxylic acid.

14. A compound of claim 1 which is the γ-lactone of 7α-(3-butenyl)-Δ⁴-17α-pregnene-17β-ol-3-one-21-carboxylic acid.

15. A compound of claim 1 which is the γ-lactone of 7α-benzyl-Δ⁴-17α-pregnene-17β-ol-3-one-21-carboxylic acid.

16. A compound of claim 1 which potassium 7α-butyl-Δ⁴-17α-pregnene-17β-ol-3-one-21-carboxylate.

17. A compound of claim 1 which potassium 7α-(3-butenyl)-Δ⁴-17α-pregnene-17β-ol-3-one-21-carboxylate.

18. A process for the preparation of a compound of claim 1 comprising reacting a compound of the formula

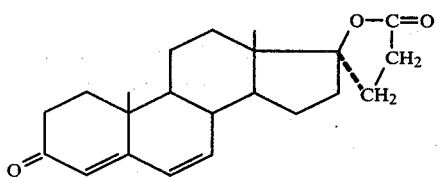

with a compound of the formula

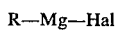

wherein R has the above definition and Hal is halogen in the presence of a cuprous salt or a compound of the formula

and then with an acid to obtain a compound of the formula

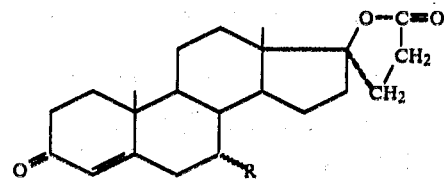

in the form of a mixture of 7α and 7β-isomers which may be optionally separated and the mixture or the individual isomers is reacted with an alkali metal hydroxide or ammonium hydroxide to obtain a compound of the formula

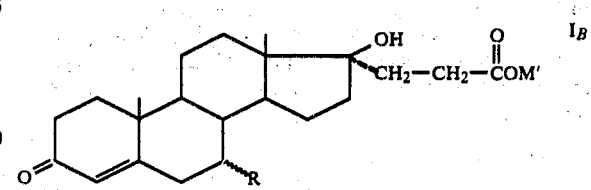

wherein R has the above definition and M' is alkali metal or NH₄ in the form of 7α- or 7β-isomers or mixtures thereof which may be optionally separated and the latter may be reacted with an acid to form the corresponding compound of formula $I_B$ wherein M' is hydrogen.

19. A composition for treatment of arterial hypertension and cardiac insufficiency comprising an effective amount of at least one compound of claim 1 for the treatment of arterial hypertension and cardiac insufficiency and an excipient.

20. A composition of claim 19 wherein X and Y form the group

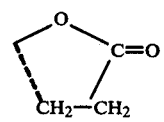

21. A composition of claim 19 wherein X is —OH and Y is

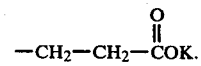

22. A composition of claim 19 wherein R is the α-position.

23. A composition of claim 19 wherein R is selected from the group consisting of ethyl, n-propyl, n-butyl, 2-methyl-propyl, allyl and vinyl.

24. A composition of claim 23 wherein R is in the α-position.

25. A composition of claim 19 wherein the compound is potassium 7α-propyl-Δ⁴-17α-pregnene-17β-one-3-one-21-carboxylate.

26. A composition of claim 19 wherein the compound is the γ-lactone of 7α-propyl-Δ⁴-17α-pregnene-17β-ol-3-one-21-carboxylic acid.

27. A method of treating arterial hypertension and cardiac insufficiencies in warm-blooded animals comprising administering to warm-blooded animals an amount of at least one compound of claim 1 sufficient to relieve cardiac insufficiencies and arterial hypertension.

28. A method of claim 27 wherein X and Y form the group

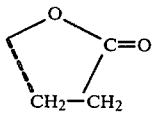

29. A method of claim 27 wherein X is —OH and Y is

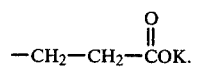

30. A method of claim 27 wherein R is in the α-position.

31. A method of claim 27 wherein R is selected from the group consisting of ethyl, n-propyl, n-butyl, 2-methylpropyl, allyl and vinyl.

32. A method of claim 31 wherein R is in the α-position.

33. A method of claim 27 wherein the compound is potassium 7α-propyl-Δ$^4$-17α-pregnene-17β-ol-3-one-21-carboxylate.

34. A method of claim 27 wherein the compouns is the γ-lactone of 7α-propyl-Δ$^4$-17α-pregnene-17β-ol-3-one-21-carboxylic acid.